(12) United States Patent
Basu et al.

(10) Patent No.: US 10,575,743 B2
(45) Date of Patent: Mar. 3, 2020

(54) HIGH ELECTRODE DENSITY BASKET CATHETER

(71) Applicant: Biosense Webster (Israel) Ltd., Yokneam (IL)

(72) Inventors: Shubhayu Basu, Anaheim, CA (US); Mario A. Solis, Rancho Cucamonga, CA (US); Asterio Pata, La Puente, CA (US); Paul Tran, San Gabriel, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 684 days.

(21) Appl. No.: 14/824,508

(22) Filed: Aug. 12, 2015

(65) Prior Publication Data

US 2015/0342532 A1 Dec. 3, 2015

Related U.S. Application Data (63) Continuation-in-part of application No. 13/860,921, filed on Apr. 11, 2013, and a continuation-in-part of application No. 14/063,477, filed on Oct. 25, 2013.

(51) Int. Cl.
*A61B 5/042* (2006.01)
*A61B 18/14* (2006.01)
(Continued)

(52) U.S. Cl.
CPC .......... *A61B 5/0422* (2013.01); *A61B 5/6858* (2013.01); *A61B 18/1492* (2013.01); *A61N 1/05* (2013.01); *A61N 1/056* (2013.01); *A61B 2017/00053* (2013.01); *A61B 2017/00526* (2013.01); *A61B 2018/0016* (2013.01); *A61B 2018/00267* (2013.01);
(Continued)

(58) Field of Classification Search
CPC . A61B 5/04085; A61B 5/0422; A61B 5/6858; A61B 2018/00267
See application file for complete search history.

(56) References Cited

U.S. PATENT DOCUMENTS

| 4,280,511 A | 7/1981 | O'Neill |
| 4,437,474 A | 3/1984 | Peers-Trevarton |

(Continued)

FOREIGN PATENT DOCUMENTS

| CN | 101888812 | 11/2010 |
| EP | 0617916 | 10/1994 |

(Continued)

OTHER PUBLICATIONS

Office Action for U.S. Appl. No. 14/063,477, dated Jun. 27, 2017.
(Continued)

*Primary Examiner* — Lee S Cohen
*Assistant Examiner* — Erin M Cardinal
(74) *Attorney, Agent, or Firm* — Dergosits & Noah LLP; Todd A. Noah (57) ABSTRACT

This disclosure is directed to a catheter having a basket-shaped electrode assembly with a high electrode density. The basket-shaped electrode assembly may have a plurality of spines, such as up to twelve, each with a plurality of electrodes, such as up to sixteen. Each spine may have cabling with embedded coiled wires such that each electrode is attached through the sheath to one of the wires.

13 Claims, 6 Drawing Sheets

(51) Int. Cl.
*A61B 5/00* (2006.01)
*A61N 1/05* (2006.01)
*A61B 18/00* (2006.01)
*A61B 17/00* (2006.01)

(52) U.S. Cl.
CPC .............. *A61B 2018/00357* (2013.01); *A61B 2218/002* (2013.01); *A61B 2562/125* (2013.01); *A61B 2562/222* (2013.01); *Y10T 29/49169* (2015.01); *Y10T 29/49174* (2015.01); *Y10T 29/49801* (2015.01)

(56) References Cited

U.S. PATENT DOCUMENTS

| | | | | |
|---|---|---|---|---|
| 4,630,611 | A | * | 12/1986 | King .................. A61B 5/076 600/377 |
| 5,016,646 | A | | 5/1991 | Gotthardt et al. |
| 5,391,199 | A | | 2/1995 | Ben-Haim |
| 5,439,485 | A | | 8/1995 | Mar |
| 5,476,495 | A | * | 12/1995 | Kordis .................. A61B 5/0422 600/374 |
| 5,555,618 | A | | 9/1996 | Winkler |
| 5,591,142 | A | | 1/1997 | Van Erp |
| 5,755,687 | A | | 5/1998 | Donlon |
| 5,772,590 | A | | 6/1998 | Webster, Jr. |
| 5,796,044 | A | | 8/1998 | Cobian et al. |
| 5,836,946 | A | | 11/1998 | Diaz |
| 5,911,739 | A | * | 6/1999 | Kordis .................. A61B 5/0422 606/41 |
| 6,004,269 | A | * | 12/1999 | Crowley .............. A61B 8/4461 600/374 |
| 6,064,905 | A | | 5/2000 | Webster et al. |
| 6,213,995 | B1 | | 4/2001 | Steen et al. |
| 6,239,724 | B1 | | 5/2001 | Doron et al. |
| 6,289,250 | B1 | | 9/2001 | Tsuboi |
| 6,332,089 | B1 | | 12/2001 | Acker et al. |
| 6,400,981 | B1 | | 6/2002 | Govari |
| 6,484,118 | B1 | | 11/2002 | Govari |
| 6,584,345 | B2 | | 6/2003 | Govari |
| 6,618,612 | B1 | | 9/2003 | Acker et al. |
| 6,690,963 | B2 | | 2/2004 | Ben-Haim et al. |
| 6,748,255 | B2 | | 6/2004 | Fuimaono et al. |
| 6,973,340 | B2 | | 12/2005 | Fuimaono et al. |
| 7,149,585 | B2 | | 12/2006 | Wessman et al. |
| 7,229,437 | B2 | | 6/2007 | Johnson |
| 7,239,922 | B1 | | 7/2007 | Boogaard et al. |
| 2002/0022782 | A1 | | 2/2002 | Kiepen et al. |
| 2002/0038139 | A1 | | 3/2002 | Wessman et al. |
| 2002/0065455 | A1 | | 5/2002 | Ben-Haim et al. |
| 2002/0143377 | A1 | | 10/2002 | Wessman et al. |
| 2003/0092303 | A1 | | 5/2003 | Osypka |
| 2003/0120150 | A1 | | 6/2003 | Govari |
| 2004/0059404 | A1 | * | 3/2004 | Bjorklund .............. A61N 1/056 607/126 |
| 2004/0068178 | A1 | | 4/2004 | Govari |
| 2006/0009404 | A1 | | 1/2006 | Williams |
| 2010/0211147 | A1 | | 8/2010 | Schiefer et al. |
| 2011/0137382 | A1 | | 6/2011 | Swanson |
| 2012/0172714 | A1 | | 7/2012 | Govari et al. |
| 2012/0172717 | A1 | | 7/2012 | Gonda |
| 2012/0271135 | A1 | | 10/2012 | Burke et al. |
| 2012/0271385 | A1 | | 10/2012 | Bernard |
| 2012/0323089 | A1 | | 12/2012 | Feer et al. |
| 2013/0150808 | A1 | | 6/2013 | Ogle et al. |
| 2013/0197616 | A1 | | 8/2013 | Dollimer et al. |
| 2014/0309512 | A1 | | 10/2014 | Govari et al. |
| 2016/0183877 | A1 | | 6/2016 | Williams et al. |

FOREIGN PATENT DOCUMENTS

| | | |
|---|---|---|
| EP | 1723981 | 11/2006 |
| EP | 2471480 | 7/2012 |
| JP | S57128805 U | 8/1982 |
| JP | H08511438 | 12/1996 |
| JP | H10510731 | 10/1998 |
| JP | 2004130114 | 4/2004 |
| JP | 2010057943 | 3/2010 |
| JP | 2012510831 | 5/2012 |
| WO | 96/05768 | 2/1996 |
| WO | 00/0062851 | 10/2000 |
| WO | 09/072039 | 6/2009 |
| WO | 09/085486 | 7/2009 |

OTHER PUBLICATIONS

Office Action for U.S. Appl. No. 14/063,477, dated Mar. 21, 2017.
Office Action for U.S. Appl. No. 14/063,477, dated Oct. 4, 2016.
Office Action for U.S. Appl. No. 13/860,921, dated Oct. 3, 2017.
Office Action for U.S. Appl. No. 13/860,921, dated Feb. 26, 2016.
Office Action for U.S. Appl. No. 13/860,921, dated Mar. 23, 2017.
Office Action for U.S. Appl. No. 13/860,921, dated Sep. 13, 2016.
Office Action for China Patent Application No. 20144233.9, dated Oct. 25, 2017.
Examination Report for Australia Patent Application No. 2014201935, dated Jun. 14, 2017.
Office Action for U.S. Appl. No. 14/063,477, dated Jan. 4, 2018.
Examination Report for Australia Patent Application No. 2014201935, dated Feb. 21, 2018.
Examination Report for Europe Patent Application No. 14190334.4, dated Feb. 28, 2018.
Notification for Reasons of Refusal for Japan Patent Application No. 2014-080835, dated Jan. 30, 2018.
European Search Report dated Jan. 12, 2017 for corresponding EP 16183699.4.
U.S. Appl. No. 13/860,921, filed Apr. 11, 2013; titled, "High Density Electrode Structure".
U.S. Appl. No. 14/063,477, filed Oct. 25, 2013; titled "Connection of Electrodes to Wires Coiled on a Core".
European Search Report dated Mar. 4, 2015 for corresponding European Application No. EP 14190334.
European Search Report dated Aug. 11, 2014 for corresponding European Application No. EP 14162843.98-1659.
Examination Report for Australia Patent Application No. 2014248091, dated Jun. 26, 2018.
Office Action for China Patent Application No. 20144233.9, dated Jun. 11, 2018.
Examination Report for European Patent Application No. 14162843.8, dated May 14, 2018.
Examination Report for European Patent Application No. 16183699.4, dated Jun. 8, 2018.
Notification for Reasons of Refusal for Japan Patent Application No. 2014-080835, dated Jun. 26, 2018.
Notification for Reasons of Refusal for Japan Patent Application No. 2014-217009, dated Aug. 7, 2018.

* cited by examiner

HIGH ELECTRODE DENSITY BASKET CATHETER

CROSS REFERENCE TO RELATED APPLICATIONS

This application is a continuation-in-part of U.S. patent application Ser. No. 13/860,921, filed Apr. 11, 2013, entitled HIGH DENSITY ELECTRODE STRUCTURE, and U.S. application Ser. No. 14/063,477, filed Oct. 25, 2013, entitled CONNECTION OF ELECTRODES TO WIRES COILED ON A CORE, the disclosures of which are hereby incorporated by reference in their entirety.

FIELD OF THE PRESENT DISCLOSURE

This invention relates to electrophysiologic (EP) catheters, in particular, EP catheters for mapping and/or ablation in the heart.

BACKGROUND

Electrophysiology catheters are commonly-used for mapping electrical activity in the heart. Various electrode designs are known for different purposes. In particular, catheters having basket-shaped electrode arrays are known and described, for example, in U.S. Pat. Nos. 5,772,590, 6,748,255 and 6,973,340, the entire disclosures of each of which are incorporated herein by reference.

Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body.

It is desirable that a basket assembly be capable of detecting in as few beats as possible, including a single beat, as much of the electrical function of the region in which the electrode assembly is deployed, such as the left or right atrium as possible. By implementing a greater number of electrodes in the electrode assembly, correspondingly greater and more complete coverage of the region may be obtained. Further, the increased number of electrodes may reduce or eliminate the need to reposition the electrode assembly to access all of the desired area in the region. However, increasing the number of electrodes may result in an undesirable increase in the overall diameter of the catheter since each electrode requires separate leads to conduct the signals being detected. As such, there is a need for a basket-shaped electrode assembly having an increased electrode density while maintaining a sufficiently minimized overall diameter to be percutaneously advanced and deployed within a chamber of a patient's heart. The techniques of this disclosure satisfy this and other needs as described in the following materials.

SUMMARY

The present disclosure is directed to a catheter with an elongated catheter body having proximal and distal ends and at least one lumen therethrough and a basket-shaped electrode assembly at the distal end of the catheter body, the basket-shaped electrode assembly comprising a plurality of spines connected at their proximal and distal ends, each spine comprising a plurality of electrodes and cabling having a corresponding plurality of wires coiled on a core and covered by a sheath such that each electrode is attached through the sheath to one of the plurality of wires, wherein the basket-shaped electrode assembly has an expanded arrangement wherein the spines bow radially outwardly and a collapsed arrangement wherein the spines are arranged generally along a longitudinal axis of the catheter body.

In one aspect, the basket-shaped electrode assembly may have at least eight, ten or twelve spines.

In one aspect, each spine may have at least ten or at least sixteen electrodes.

For example, the basket-shaped electrode assembly may have at least twelve spines and each spine may have at least sixteen electrodes with the catheter body having a diameter less than approximately 10 french.

In one aspect, each spine may have a concave distal region, a convex middle region and a concave proximal region.

In one aspect, the catheter may have a cap securing the distal ends of each spine, wherein opposing spines are formed by a continuous piece of material routed through apertures in the cap.

In one aspect, the catheter may also include an expander having proximal and distal ends, the expander slidably disposed within the lumen and aligned with the longitudinal axis of the catheter body, wherein the plurality of spines are attached at their distal ends to the expander, such that the basket-shaped electrode assembly has the expanded arrangement when the expander is moved proximally along the longitudinal axis relative to the catheter body and has the collapsed arrangement when the expander is moved distally along the longitudinal axis relative to the catheter body.

In one aspect, each spine may have a flexible wire disposed within the core of the cabling. Further, the flexible wire may be a shape memory alloy.

In one aspect, the lumen of the catheter may be configured to deliver irrigation fluid to the basket-shaped electrode assembly.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to obtain the 'picture' as quickly as possible, such as within one heartbeat. In other words, all the points of the map or picture may be obtained simultaneously within one-tenth of a second. According to the techniques of this disclosure, a basket-shaped electrode assembly having a high electrode density may be used to accurately map this electrical activity.

Figure 1:
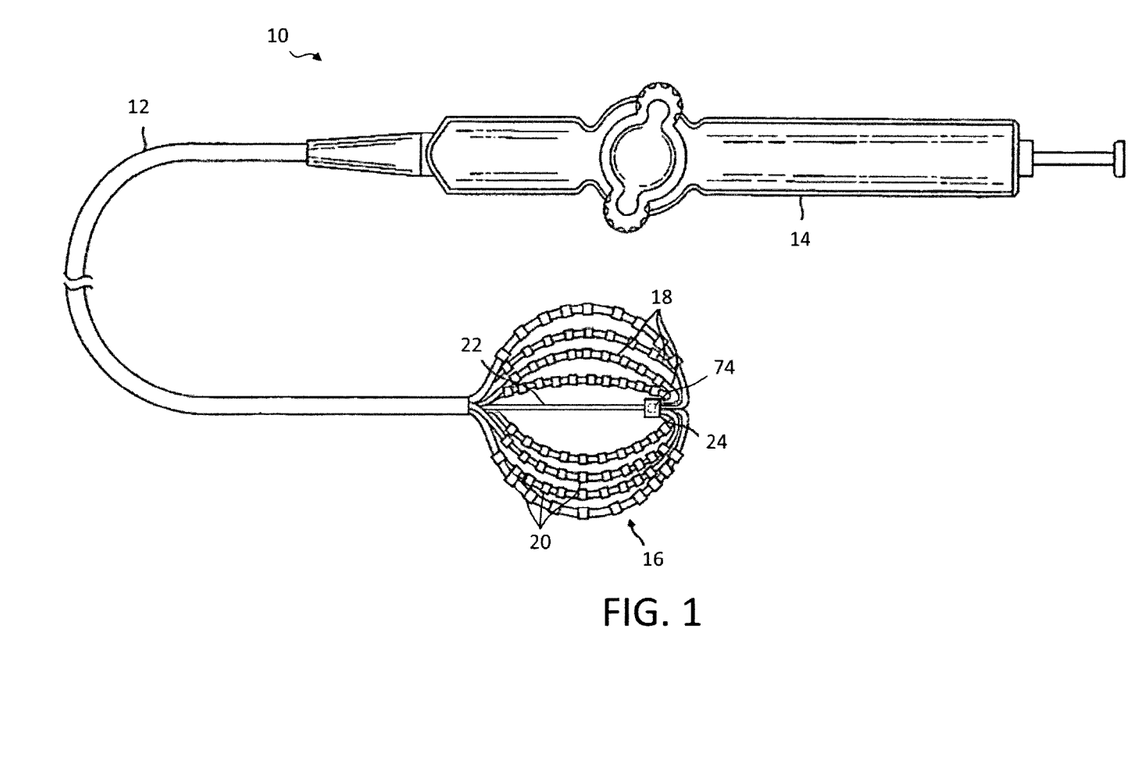
FIG. 1 is a top plan view of a catheter of the present invention, according to one embodiment.

As shown in FIG. 1, the catheter 10 comprises an elongated catheter body 12 having proximal and distal ends and a control handle 14 at the proximal end of the catheter body, with a basket-shaped electrode assembly 16 having a plurality of spines 18, each carrying multiple electrodes 20, mounted at the distal end of the catheter body 12. The catheter body 12 comprises an elongated tubular construction having a single, axial or central lumen (not shown), but can optionally have multiple lumens if desired. To enable accurate mapping of electrical signals, for example to detect most or substantially all of the electrical function of the right or left atrium in as little as a single heartbeat, it may be desirable to provide an array of electrodes with a relatively high density. As such, numbers of spines 18 employed may be eight, ten, twelve or any other suitable number. Spines 18 may be evenly or unevenly distributed radially. Further, each spine 18 may include multiple electrodes 20, such as at least ten and up to approximately 16 electrodes per spine. Similarly, the electrodes may be evenly distributed along the spine or may be skewed proximally, centrally or distally to facilitate analysis of the measured electrical signals.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. The outer diameter of the catheter body 12 is not critical, but generally should be as small as possible and may be no more than about 10 french depending on the desired application. In one aspect, the overall diameter of the catheter body 12 may relate to the number of electrodes 20 implemented by basket-shaped electrode assembly 16 in order to accommodate the associated electrical leads. For example, a twelve-spine design with each spine carrying sixteen electrodes for a total of 192 electrodes, a ten-spine design with each spine carrying sixteen electrodes for a total of 160 electrodes and an eight-spine design with each spine carrying sixteen electrodes for a total of 128 electrodes may utilize up to a 10.0 french catheter body. Likewise the thickness of the outer wall is not critical, but may be thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

The basket-shaped electrode assembly 16 may also include an expander 22 is generally coaxial with the catheter body 12 and extends from the proximal end of catheter body 12 through the central lumen and is attached, directly or indirectly, to the distal ends of spines 18. The expander 22 is afforded longitudinal movement relative to the catheter body so that it can move the distal ends of the spines 18 proximally or distally relative to the catheter body 12 to radially expand and contract, respectively, the electrode assembly. Since the proximal ends of spines 18 are secured to the catheter body 12, relative movement of expander 22 in the proximal direction shortens the distance between the distal and proximal ends of spines 18, causing them to bow outwards into an expanded arrangement. The expander 22 comprises a material sufficiently rigid to achieve this function. Alternatively or in addition, spines 18 may include a material as described below that facilitates assuming the expanded arrangement, such as a shape memory material, so that expander 22 may be omitted or may be used to aid the transition between the expanded and collapsed arrangements. In an embodiment, the expander 22 may comprise a wire or hypotube formed from a suitable shape memory material, such as a nickel titanium alloy as described below. As will be appreciated, different relative amounts of movement of the expander 22 along the longitudinal axis may affect the degree of bowing, such as to enable the spines 18 to exert greater pressure on the atrial tissue for better contact between the tissue and the electrodes on the spines. Thus, a user can change the shape of the electrode assembly by adjusting the longitudinal extension or withdrawal of the expander.

Alternatively or in addition, spines 18 may include a material as described below that facilitates assuming the expanded arrangement, so that expander 22 may be omitted or may be used to aid the transition between the expanded and collapsed arrangements.

Figure 2:
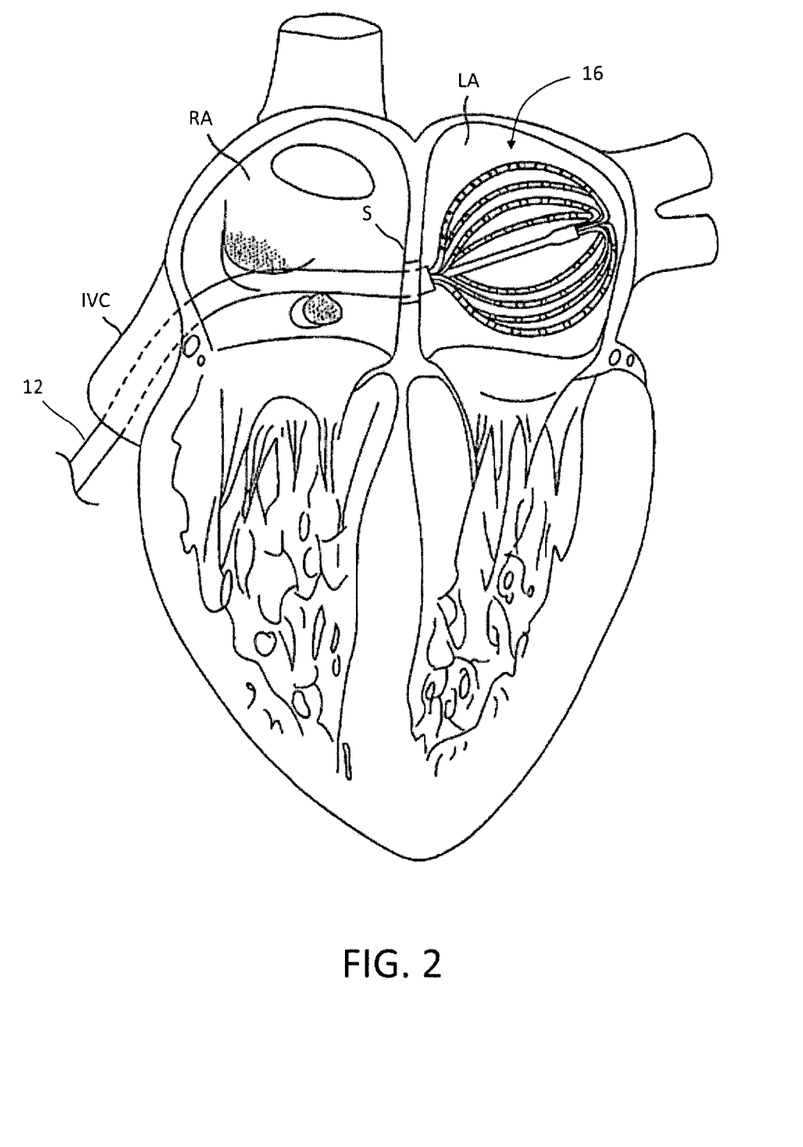
FIG. 2 is a schematic view of the basket-shaped electrode assembly of FIG. 1 deployed in the left atrium.

As shown in FIG. 2, when the basket-shaped electrode assembly 16 assumes the expanded configuration, spines 18 bow outwards into contract or closer proximity with the walls of the chamber in which it has been deployed, such as the left atrium. Correspondingly, relative movement of expander 22 in the distal direction lengthens the distance between the distal and proximal ends of spines 18, causing them to assume a generally linear configuration in line with the catheter body 12 to minimize their outer diameter for insertion within and withdrawal from the patient.

In one aspect, an electrophysiologist may introduce a guiding sheath, guidewire and dilator into the patient, as is generally known in the art. As an example, a suitable guiding sheath for use in connection with the inventive catheter is a 10 french DiRex™ Guiding Sheath (commercially available from BARD, Murray Hill, N.J.). The guidewire is inserted, the dilator is removed, and the catheter is introduced through the guiding sheath whereby the guidewire lumen in the expander permits the catheter to pass over the guidewire. In one exemplary procedure as depicted in FIG. 2, the catheter is first introduced to the right atrium (RA) via the inferior vena cava (IVC), where it passes through the septum (S) in order to reach the left atrium (LA).

As will be appreciated, the guiding sheath covers the spines 18 of the basket-shaped electrode assembly 16 in a collapsed position so that the entire catheter can be passed through the patient's vasculature to the desired location. The expander 22 may be positioned distally of the catheter body to allow the spines of the assembly to be flattened while the assembly is passed through the guiding sheath. Once the distal end of the catheter reaches the desired location, e.g., the left atrium, the guiding sheath is withdrawn to expose the basket-shaped electrode assembly 16. The expander 22 is drawn proximally or otherwise manipulated so that the spines 18 flex outwardly between the distal and proximal junctions. With the basket-shaped electrode assembly 16 radially expanded, the ring electrodes 20 contact atrial tissue. As recognized by one skilled in the art, the basket-shaped electrode assembly 16 may be fully or partially expanded, straight or deflected, in a variety of configurations depending on the configuration of the region of the heart being mapped.

When the basket-shaped electrode assembly 16 is expanded, the electrophysiologist may map local activation time and/or ablate using electrodes 20, which can guide the electrophysiologist in diagnosing and providing therapy to the patient. The catheter may include one or more reference ring electrodes mounted on the catheter body and/or one or more reference electrodes may be placed outside the body of the patient. By using the inventive catheter with the multiple electrodes on the basket-shaped electrode assembly, the electrophysiologist can obtain a true anatomy of a cavernous region of the heart, including an atrium, by measuring less points than with traditional catheters, allowing a more rapid mapping of the region.

As used herein, the term "basket-shaped" in describing the electrode assembly 16 is not limited to the depicted configuration, but can include other designs, such as spherical or egg-shaped designs, that include a plurality of expandable arms or spines connected, directly or indirectly, at their proximal and distal ends. In one aspect, different sized basket-shaped electrode assemblies may be employed depending on the patient's anatomy to provide a close fit to the area of the patient being investigated, such as the right or left atria.

Figure 3:
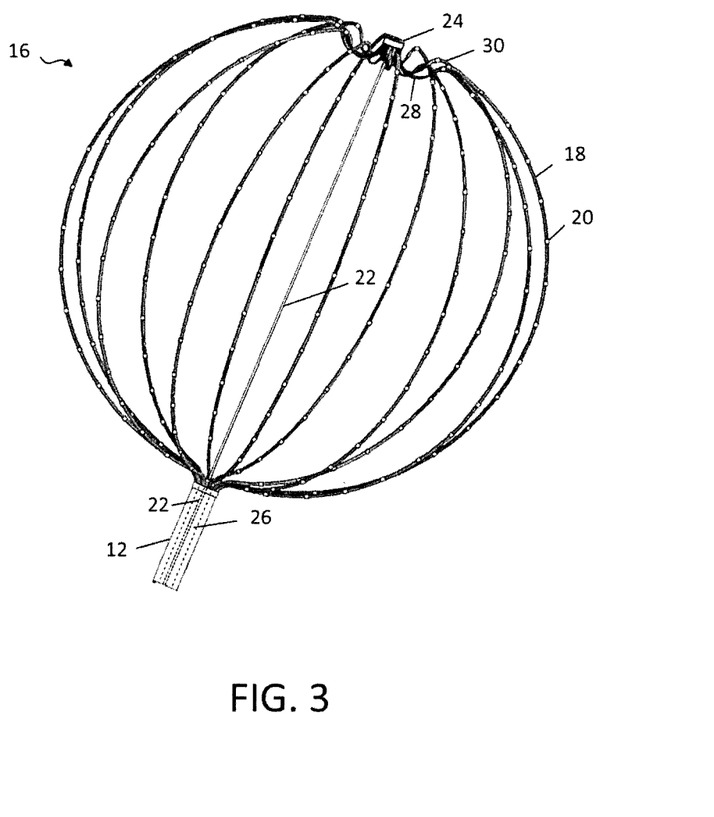
FIG. 3 is a schematic view of a basket-shaped electrode assembly, according to one embodiment.

A detailed view of one embodiment of the basket-shaped electrode assembly 16 is shown in FIG. 3, featuring a total of twelve spines 18, each carrying sixteen electrodes 20. As noted above, in other embodiments, different numbers of spines 18 and/or electrodes 20 may be employed, each of which may be evenly or unevenly distributed as desired. The distal ends of the spines 18 and the expander 22 may be secured to a distal cap 24. Correspondingly, the proximal ends of the spines 18 may be secured to the distal end of the catheter body 12, while the expander 22 may be routed through lumen 26 of the catheter body 12 so that the proximal end extends to the control handle 14. In some embodiments, lumen 26 may also be used to supply a suitable irrigation fluid, such as heparinized saline, to the basket-shaped electrode assembly 16. A fitting (not shown) in the control handle 14 may be provided to conduct irrigation fluid from a suitable source or pump into the lumen 26.

Each spine 18 may comprise a flexible wire 28 with a non-conductive covering 30 on which one or more of the ring electrodes 20 are mounted. In an embodiment, the flexible wires 28 may be formed from a shape memory material to facilitate the transition between expanded and collapsed arrangements and the non-conductive coverings 30 may each comprise a biocompatible plastic tubing, such as polyurethane or polyimide tubing. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, the basket-shaped electrode assembly 16 may have a three dimensional shape that can be easily collapsed to be fed into a guiding sheath and then readily returned to its expanded shape memory configuration upon delivery to the desired region of the patient upon removal of the guiding sheath.

Alternatively, in some embodiments the spines 18 can be designed without the internal flexible wire 28 if a sufficiently rigid nonconductive material is used for the non-conductive covering 30 to permit radial expansion of the basket-shaped electrode assembly 16, so long as the spine has an outer surface that is non-conductive over at least a part of its surface for mounting of the ring electrodes 20.

Figure 4:
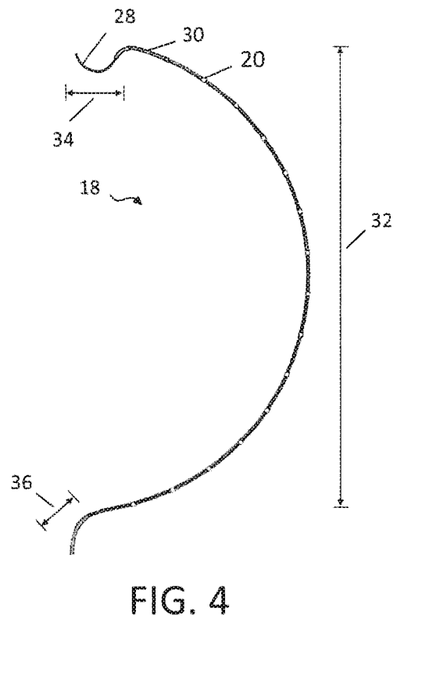
FIG. 4 is a schematic view of one spine of the basket-shaped electrode assembly of FIG. 3.

A single spine 18 is shown in its expanded, shape memory configuration in FIG. 4. In this embodiment, spine 18 has a middle region 32 having a convex shape configured to bring electrodes 20 into contact or close proximity with the wall of the chamber in which it has been positioned. As noted above, the flexible wire 28 has non-conductive covering 30 on which the electrodes 20 are positioned. A distal region 34 may exhibit a concave configuration, positioned generally within a radius of curvature indicated by the middle region 32. This configuration provides the distal region 34 with a smooth transition from the flexible wire 28 being aligned with the longitudinal axis of catheter body 12 to an apex joining the middle region 32. Alignment with the longitudinal axis allows for a minimized collapsed diameter, while the concave shape allows one or more electrodes 20 to be positioned near the apex to provide sensor coverage for the polar region adjacent the distal cap 24. A proximal region 36 may have a concave configuration, positioned generally outside the radius of curvature indicated by the middle region 32. Similarly, this configuration provides a smooth transition from the middle region 32 to the flexible wire again being in alignment with the longitudinal axis.

Figure 5:
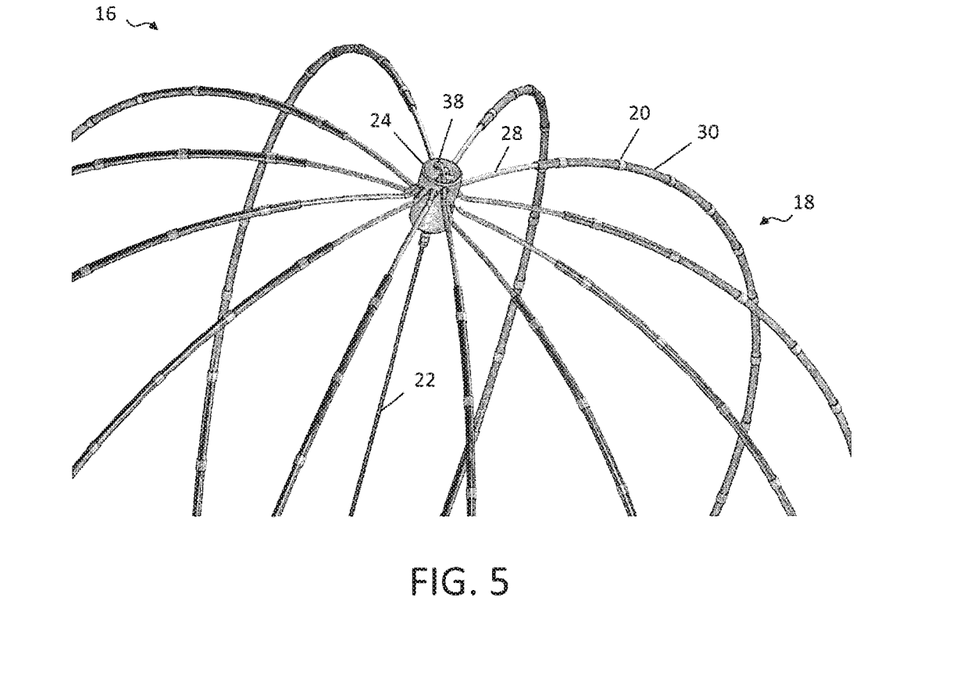
FIG. 5 is a schematic view of another basket-shaped electrode assembly, according to one embodiment.

Another exemplary embodiment is shown in FIG. 5. In this design, opposing spines 18 are formed by a continuous stretch of flexible wire 28 extending through apertures 38 configured as through holes in the generally cylindrical distal cap 24. Apertures 38 may be offset in a helical pattern as shown or in any other suitable manner to accommodate each loop of flexible wire 28 without interference from each other. As will be appreciated, the position of each spine may be stabilized with respect to its opposing spine since they are formed from a single piece of wire.

Figure 6A:
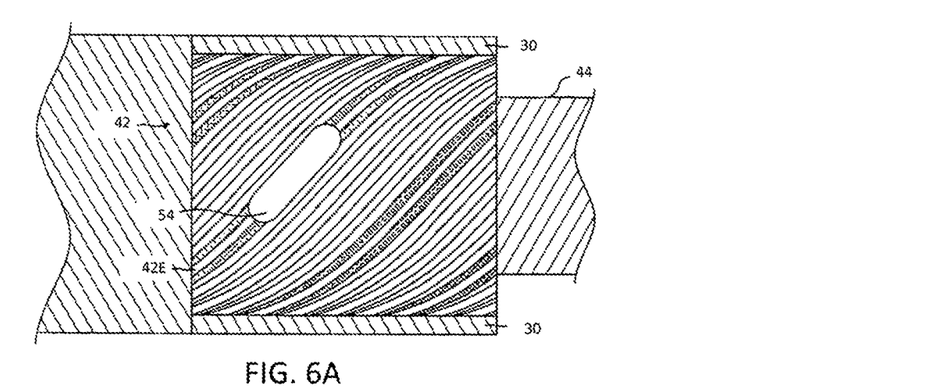
FIG. 6A is a top view of a cabling of a spine of a basket-shaped electrode assembly with part(s) broken away, according to one embodiment.
Figures 6B, 6C:
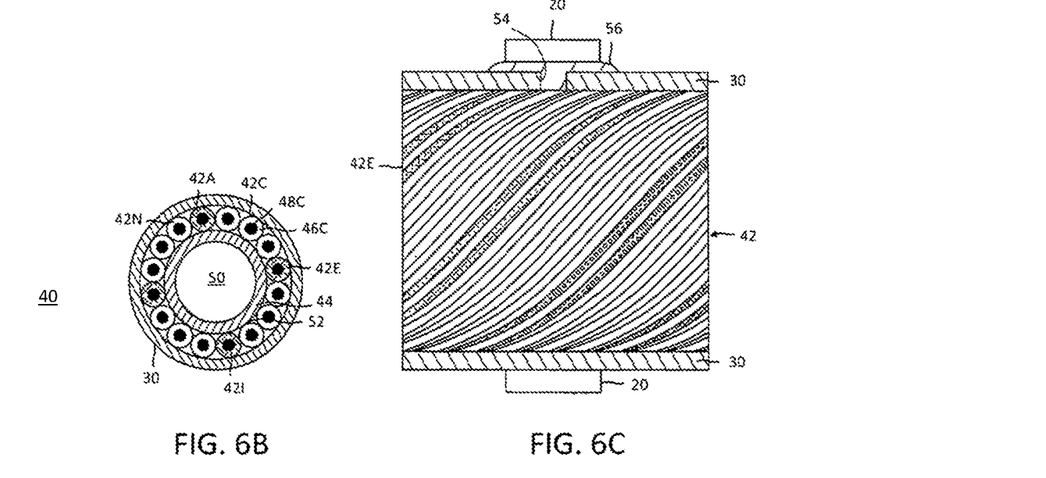
FIG. 6B is an end cross-sectional view of the cabling of FIG. 6A.
FIG. 6C is a side view of the cabling of FIG. 6A, with part(s) broken away.

In a further aspect, each spine 18 may include cabling 40 with built-in or embedded lead wires 42 for the electrodes 20 carried by the spine as shown in FIGS. 6A-C. The cabling has a core 44, and a plurality of generally similar wires 42 each covered by an insulating layer 46 that enables each wire to be formed and to function as a conductor 48. The core 44 provides a lumen 50 in which can pass other components such as a support structure in the form of flexible wire 28 and/or additional lead wire(s), cables, tubing or other components.

In the following description, generally similar components associated with cabling 40 are referred to generically by their identifying component numeral, and are differentiated from each other, as necessary, by appending a letter A, B, . . . to the numeral. Thus, wire 42C is formed as conductor 48C covered by insulating layer 46C. While embodiments of the cabling may be implemented with substantially any plurality of wires 42 in the cabling, for clarity and simplicity in the following description cabling 40 is assumed to comprise N wires 42A, 42B, 42C, . . . 42N, where N equals at least the number of ring electrodes on each respective spine 18 of the basket-shaped electrode assembly 16. For purposes of illustration, insulating layers 46 of wires 42 have been drawn as having approximately the same dimensions as conductors 48. In practice, the insulating layer is typically approximately one-tenth the diameter of the wire.

The wires 42 are formed over an internal core 44, which is typically shaped as a cylindrical tube. The core material is typically selected to be a thermoplastic elastomer such as a polyether block amide or PEBAX®. Wires 42 are formed on an outer surface 52 of the core 44 by coiling the wires around the tube. In coiling wires 42 on the surface 52, the wires are arranged so that they contact each other in a "close-packed" configuration. Thus, in the case that core 44 is cylindrical, each wire 42 on the outer surface is in the form of a helical coil, configured in a multi-start thread configuration. For example, in the case of the N wires 42 assumed herein, wires 42 are arranged in an N-start thread configuration around core 44.

In contrast to a braid, all helical coils of wires 42 herein have the same handedness (direction of coiling). Moreover, wires in braids surrounding a cylinder are interleaved, so are not in the form of helices. Because of the non-helical nature of the wires in braids, even braid wires with the same handedness do not have a threaded form, let alone a multi-start thread configuration. Furthermore, because of the lack of interleaving in arrangements of wires in embodiments of the cabling, the overall diameter of the cabling produced is less than that of cabling using a braid, and the reduced diameter is particularly beneficial when the cabling is used for a catheter.

Once wires 42 have been formed in the multi-start thread configuration described above, the wires are covered with a protective sheath, such as in the form of the non-conductive covering 30 described above. The protective sheath material is typically selected to be a thermoplastic elastomer such as for example, 55D PEBAX without additives so that it is transparent. In that regard, the insulating layer 46 of at least one of wires 42 may be colored differently from the colors of the remaining wires as an aid in identifying and distinguishing the different wires.

The process of coiling wires 42 around the core 44, and then covering the wires by the non-conductive covering 30 essentially embeds the wires within a wall of cabling 40, the wall comprising the core and the sheath. Embedding the wires within a wall means that the wires are not subject to mechanical damage when the cabling is used to form a catheter. Mechanical damage is prevalent for small wires, such as 48AWG wires, if the wires are left loose during assembly of a catheter.

In use as a catheter, an approximately cylindrical volume or lumen 50 enclosed by the core 44, that is afforded by embedding smaller wires (such as the 48 AWG wires) in the wall, allows at least a portion of the lumen 50 to be used for other components. It is understood that the plurality of wires 42 shown in the drawings is representative only and that a suitable cabling provides at least a plurality of wires equal to or greater than the plurality of ring electrodes mounted on each cabling or spine of the assembly. Cabling suitable for use with the present invention is described in U.S. application Ser. No. 13/860,921, filed Apr. 11, 2013, entitled HIGH DENSITY ELECTRODE STRUCTURE, and U.S. application Ser. No. 14/063,477, filed Oct. 25, 2013, entitled CONNECTION OF ELECTRODES TO WIRES COILED ON A CORE, the entire disclosures of which have been incorporated above. Each cabling 40 (with embedded lead wires 42) may extend to the control handle 14 for suitable electrical connection of wires 42, thereby allowing signals measured by electrodes 20 to be detected.

As noted, each spine 18 and cabling 40 pair carries a plurality of ring electrodes 20, which may be configured as monopolar or bipolar, as known in the art. Cabling 40 is schematically shown by a top view in FIG. 6A and by a side view in FIG. 6C, in which portions of non-conductive covering 30 have been cut away to expose wires 42 of the cabling 40, as well as to illustrate the attachment of a ring electrode 20 to the cabling 40. FIG. 6A illustrates cabling 40 prior to attachment of electrode 20, while FIG. 6C illustrates the cabling after the ring electrode has been attached. The ring electrodes 20 may have suitable dimensions to allow them to be slid over non-conductive covering 30.

The attachment point for each electrode 20 may be positioned over one or more of the wires 42, such as wire 42E in the illustrated example. A section of non-conductive covering 30 above the wire 42E and a corresponding section of insulating layer 46E are removed to provide a passage 54 to conductor 48E. In a disclosed embodiment, conductive cement 56 may be fed into the passage, ring electrode 20 may then be slid into contact with the cement, and finally the electrode may be crimped in place. Alternatively, the ring electrode 20 may be attached to a specific wire 42 by pulling the wire through non-conductive covering 30, and resistance welding or soldering the ring electrode to the wire.

Figure 7:
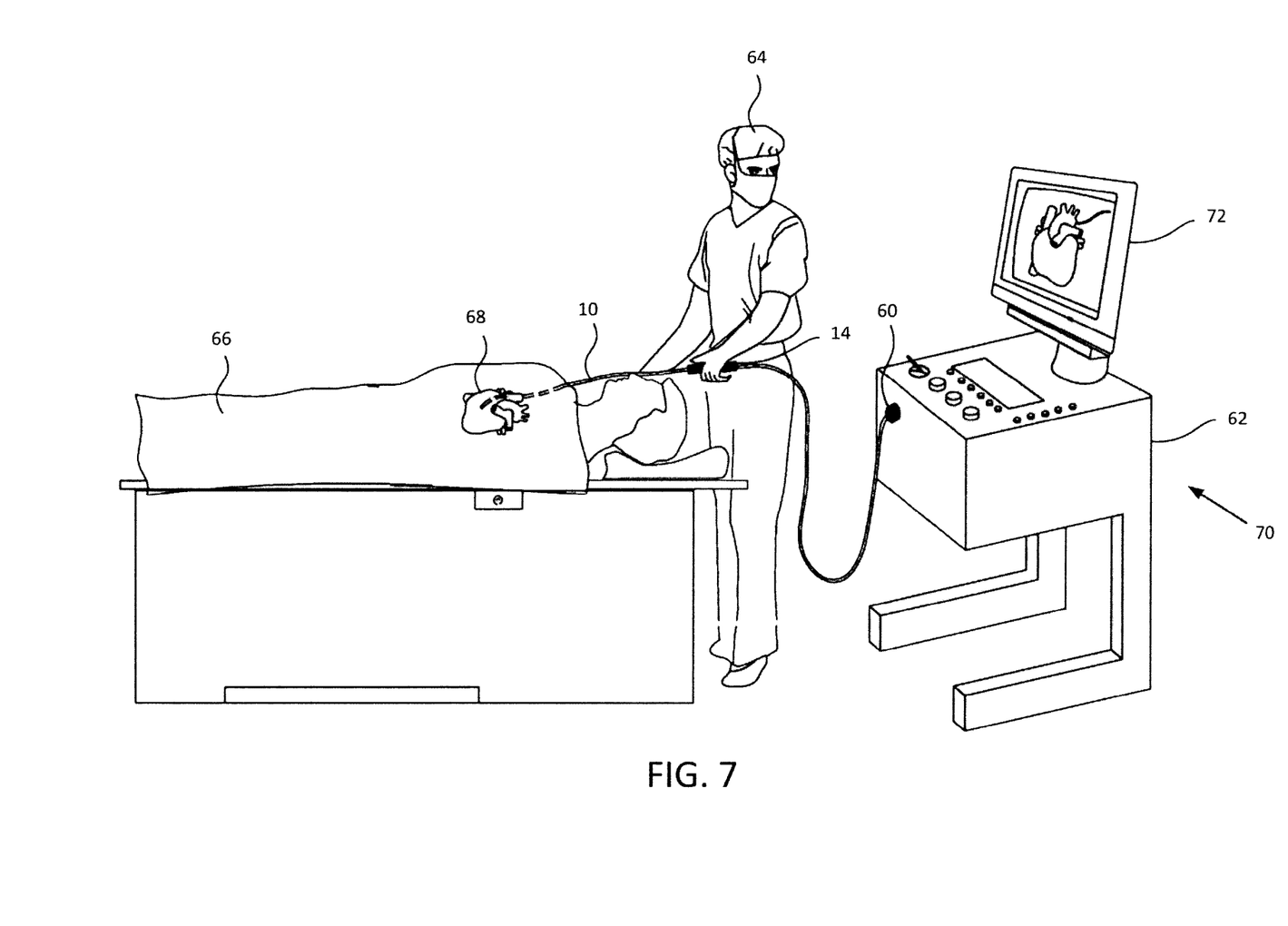
FIG. 7 is a schematic illustration of an invasive medical procedure using a basket-shaped electrode assembly, according to one embodiment.

To help illustrate use of the basket-shaped electrode assembly 16, FIG. 7 is a schematic depiction of an invasive medical procedure, according to an embodiment of the present invention. Catheter 10, with the basket-shaped electrode assembly 16 (not shown in this view) at the distal end may have a connector 60 at the proximal end for coupling the wires 42 from their respective electrodes 20 (neither shown in this view) to a console 62 for recording and analyzing the signals they detect. An electrophysiologist 64 may insert the catheter 10 into a patient 66 in order to acquire electropotential signals from the heart 68 of the patient. The professional uses the control handle 14 attached to the catheter in order to perform the insertion. Console 62 may include a processing unit 70 which analyzes the received signals, and which may present results of the analysis on a display 72 attached to the console. The results are typically in the form of a map, numerical displays, and/or graphs derived from the signals.

In a further aspect, the processing unit 70 may also receive signals from one or more location sensors 74 provided near a distal end of the catheter 10 adjacent the basket-shaped electrode assembly 16 as schematically indicated in FIG. 1. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 70 to determine the position, (e.g., the location and orientation) of the distal end of catheter 10 within the heart cavity. The electrophysiologist may then view the position of the basket-shaped electrode assembly 16 on an image the patient's heart on the display 72. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally of the basket-shaped electrode assembly 16. The coordinates of the distal sensor relative to the proximal sensor may be determined and, with other known information pertaining to the curvature of the spines 18 of the basket-shaped electrode assembly 16, used to find the positions of each of the electrodes 20.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising an elongated catheter body having proximal and distal ends and at least one lumen therethrough and a basket-shaped electrode assembly at the distal end of the catheter body, the basket-shaped electrode assembly comprising a plurality of spines connected at their proximal and distal ends, each spine comprising a plurality of electrodes and cabling having a corresponding plurality of wires coiled on a core, the plurality of wires coiled on the core in a single layer arranged in a close-packed configuration such that the wires contact each other and covered by a sheath such that each electrode is attached through the sheath to one of the plurality of wires, wherein the basket-shaped electrode assembly has an expanded arrangement wherein the spines bow radially outwardly and a collapsed arrangement wherein the spines are arranged generally along a longitudinal axis of the catheter body.

2. The catheter of claim 1, wherein the basket-shaped electrode assembly comprises at least eight spines.

3. The catheter of claim 1, wherein the basket-shaped electrode assembly comprises at least ten spines.

4. The catheter of claim 1, wherein the basket-shaped electrode assembly comprises at least twelve spines.

5. The catheter of claim 1, wherein each spine comprises at least ten electrodes.

6. The catheter of claim 1, wherein each spine comprises at least sixteen electrodes.

7. The catheter of claim 1, wherein the basket-shaped electrode assembly comprises at least twelve spines, each spine comprises at least sixteen electrodes and the catheter body has a diameter less than approximately 10 french.

8. The catheter of claim 1, wherein each spine has a concave distal region, a convex middle region and a concave proximal region.

9. The catheter of claim 1, further comprising a cap securing the distal ends of each spine, wherein opposing spines are formed by a continuous piece of material routed through apertures in the cap.

10. The catheter of claim 1, further comprising an expander having proximal and distal ends, the expander slidably disposed within the lumen and aligned with the longitudinal axis of the catheter body, wherein the plurality of spines are attached at their distal ends to the expander, such that the basket-shaped electrode assembly has the expanded arrangement when the expander is moved proximally along the longitudinal axis relative to the catheter body and has the collapsed arrangement when the expander is moved distally along the longitudinal axis relative to the catheter body.

11. The catheter of claim 1, wherein each spine further comprises a flexible wire disposed within the core of the respective cabling.

12. The catheter of claim 11, wherein each flexible wire is a shape memory alloy.

13. The catheter of claim 1, wherein the lumen is configured to deliver irrigation fluid to the basket-shaped electrode assembly.

* * * * *